(12) United States Patent
Dancer et al.

(10) Patent No.: US 7,560,576 B2
(45) Date of Patent: Jul. 14, 2009

(54) CRYSTALLINE BASE OF ESCITALOPRAM AND ORODISPERSIBLE TABLETS COMPRISING ESCITALOPRAM BASE

(75) Inventors: Robert Dancer, Hvidovre (DK); Hans Petersen, Vanlose (DK); Ole Nielsen, Valby (DK); Michael Harold Rock, Hvidovre (DK); Helle Eliasen, Koge (DK); Ken Liljegren, Vaerlose (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 12/046,984

(22) Filed: Mar. 12, 2008

(65) Prior Publication Data

US 2008/0161388 A1   Jul. 3, 2008

Related U.S. Application Data

(62) Division of application No. 11/425,522, filed on Jun. 21, 2006.

(60) Provisional application No. 60/693,214, filed on Jun. 22, 2005.

(51) Int. Cl.
C07D 307/00 (2006.01)
A61K 31/34 (2006.01)

(52) U.S. Cl. .................... 549/467; 514/469
(58) Field of Classification Search .......... 549/467; 514/469
See application file for complete search history.

(56) References Cited

U.S. PATENT DOCUMENTS

| 4,943,590 A | 7/1990 | Boegesoe et al. |
| RE34,712 E | 8/1994 | Boegesoe et al. |
| 5,607,697 A | 3/1997 | Alkire et al. |
| 2004/0167209 A1 | 8/2004 | Dancer et al. |

FOREIGN PATENT DOCUMENTS

| AU | 2003282383 | 6/2005 |
| DE | 2657013 | 7/1977 |
| DE | 200 07 303 | 8/2000 |
| DE | 60202216 | 1/2003 |
| DE | 60217932 | 4/2005 |
| DE | 60202794 | 5/2006 |
| EP | 347066 | 12/1989 |
| EP | 0347066 | 12/1989 |
| EP | 1346989 | 9/2003 |
| JP | 2003527383 | 9/2003 |
| JP | 2004536093 | 12/2004 |
| WO | 98/19512 A2 | 5/1998 |
| WO | 98/19513 | 5/1998 |
| WO | 99/00548 | 1/1999 |
| WO | 00/11926 A2 | 3/2000 |
| WO | 00/13648 A2 | 3/2000 |
| WO | WO-0108619 | 2/2001 |
| WO | 01/47877 A1 | 7/2001 |
| WO | 01/68627 | 9/2001 |
| WO | WO-0168627 | 9/2001 |
| WO | 03/000672 | 1/2003 |
| WO | 03/006449 A1 | 1/2003 |
| WO | WO-03/000672 | 1/2003 |
| WO | 03/011278 | 2/2003 |
| WO | WO-03039520 | 5/2003 |
| WO | 03/051861 A1 | 6/2003 |
| WO | 03/092659 | 11/2003 |
| WO | 2004/056791 A1 | 7/2004 |
| WO | 2005/018617 A1 | 3/2005 |
| WO | WO-2005049596 | 6/2005 |
| WO | 2006/106531 | 10/2006 |

OTHER PUBLICATIONS

P. Molander et al., Journal of Chromatography, B: Analytical Technologies in the Biomedical and Life Sciences (2002), 766(1), 77-87) discloses citalopram N-oxide (p. 79, column A, first paragraph, line 10.*
Partial International Search Report dated Jan. 16, 2007 issued for corresponding International Patent Application No. PCT/DK2006/000366.

* cited by examiner

*Primary Examiner*—D. Margaret Seaman
*Assistant Examiner*—Nizal S Chandrakumar
(74) *Attorney, Agent, or Firm*—Darby & Darby P.C.

(57) ABSTRACT

The present invention relates to the crystalline base of the well known antidepressant drug escitalopram, S-1-[3-(dimethylamino)propyl]-1-(4-fluorophenyl)-1,3-dihydro-5-isobenzofurancarbonitrile, formulations of said base, a process for the preparation of purified salts of escitalopram, such as the oxalate, using the base, the salts obtained by said process and formulations containing such salts, and a process for the preparation of purified escitalopram free base or salts of escitalopram, such as the oxalate, using the hydrobromide, the salts obtained by said process and formulations containing such salts. Finally the present invention relates to an orodispersible tablet having a hardness of at least 22 N and an oral-disintegration time of less than 120 s and comprising an active pharmaceutical ingredient adsorbed onto a water soluble filler wherein the active pharmaceutical ingredient has a melting point in the range of 40-100° C., as well as a method for making such an orodispersible tablet.

1 Claim, No Drawings

CRYSTALLINE BASE OF ESCITALOPRAM AND ORODISPERSIBLE TABLETS COMPRISING ESCITALOPRAM BASE

This application is a divisional of U.S. patent application Ser. No. 11/425,522, filed Jun. 21, 2006, which claims the benefit of U.S. Provisional Application Ser. No. 60/693,214, filed Jun. 22, 2005, all of which are hereby incorporated by reference.

The present invention relates in a first aspect to the crystalline base of the well known anti-depressant drug escitalopram, S-1-[3-(dimethylamino)propyl]-1-(4-fluorophenyl)-1, 3-dihydro-5-isobenzofurancarbonitrile, formulations of said base, processes for the preparation of purified escitalopram free base and salts thereof, using the crystalline base or hydrobromide of escitalopram, the salts obtained by said process and formulations containing such salts. In a second aspect the present invention relates to orodispersible tablets comprising an active pharmaceutical ingredient adsorbed onto a water-soluble filler wherein said active pharmaceutical ingredient has a melting point in the range of 40-100° C., and methods for the manufacture of such orodispersible tablets.

BACKGROUND OF THE INVENTION

Escitalopram is a well-known antidepressant drug that has now been on the market for some years and has the following structure:

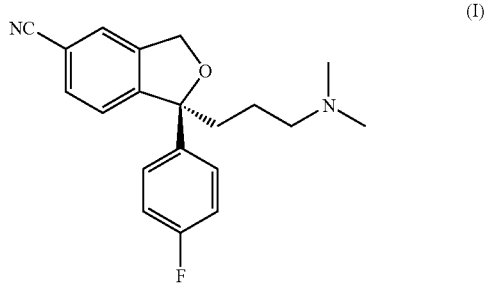

It is a selective, centrally-acting serotonin (5-hydroxytryptamine; 5-HT) reuptake inhibitor, accordingly having antidepressant activities.

Escitalopram was first disclosed in U.S. Pat. No. 4,943, 590. The escitalopram prepared was isolated as the oxalate. Furthermore, the escitalopram base was obtained as an oil. Escitalopram is marketed as the oxalate.

Escitalopram may inter alia be prepared according to the processes disclosed in WO 2003006449 and WO 2003051861.

Crystalline escitalopram hydrobromide was disclosed in WO 2004056791.

Orodispersible tablets have gained considerable attention over the last years. Orodispersible tablets disintegrate in the mouth and are, subsequently, swallowed. This is advantageous for patients having difficulties swallowing conventional tablet formulations and, consequently, orodispersible tablets increase not only patient convenience but also patient compliance. The active pharmaceutical ingredient that is incorporated in the fast disintegrating tablet may partly or completely dissolve in the mouth, thereby enabling absorption to take place from the oral cavity.

In literature, several terms have been applied for orodispersible tablets. Amongst these are fast dissolving tablets, fast dispersing tablets, fast disintegrating tablets, melt tablets, rapid dissolve tablets, rapid-melt tablets, mouth-dissolving tablets, quick-disintegrating tablets.

Various methods have been applied to manufacture fast disintegrating tablets. Many of the methods make use of unconventional equipment and complicated processing techniques such as lyophilization and foam techniques. Many of these methods result in fast disintegrating tablets with poor tablet strength and low friability. This may prevent the use of conventional packaging material and conventional packaging procedures.

WO2005/018617 discloses the use of conventional melt granulation to produce granules from a low melting point compound that melts or soften at or below 37° C., and a water-soluble excipient. The granules were subsequently mixed with active pharmaceutical ingredient and additional excipients and then compressed to yield fast dissolving tablets of low hardness, 2.2 kP or less.

Manufacturing methods that are based on the use of conventional equipment and techniques and that result in fast disintegrating tablets with sufficient strength are therefore desirable.

It has now been found that the base of escitalopram may be obtained as a very pure crystalline product, which may easily be handled and formulated conveniently into tablets and other pharmaceutical forms. Furthermore, it has been found that an efficient purification of escitalopram may be obtained during manufacture of escitalopram (e.g. of the oxalate salt) by crystallising the base, and thereafter optionally forming a salt from the base.

It has likewise been found that a very efficient purification of escitalopram may be obtained during manufacture of escitalopram (e.g. of the free base or the oxalate salt) by crystallising the hydrobromide, and thereafter optionally forming the base or a salt, which is not the hydrobromide, from the base.

These purification processes are particularly useful for removing intermediates which are structurally closely related to escitalopram, in particular compounds which only differ from escitalopram by the substituent situated in position 5 on the isobenzofurane ring and/or in lacking one or both of the methyl groups, and intermediates which have physical/chemical properties which are close to those of escitalopram, e.g. the 1-[3-(dimethylamino)propyl]-1-(4-fluorophenyl)-1, 3-dihydro-isobenzofuranes having halogen (in particular bromide and chloride), an amide or an ester in position 5 of the isobenzofurane ring, or the compounds of formula (III).

Furthermore, a novel type of orodispersible tablets with high strength and low friability has been developed. These novel orodispersible tablets can be manufactured in a melt agglomeration process, melt coating process or melt extrusion process that can be performed using conventional melt agglomeration equipment or melt extrusion equipment. In the process the active pharmaceutical ingredient is heated to a temperature above, around or slightly below the melting point to melt agglomerate or melt coat filler particles. The agglomerates or the coated filler particles are, subsequently, mixed with suitable excipients and compressed into tablets.

Escitalopram base has been found to be suitable for formulation in such orodispersible tablets.

SUMMARY OF THE INVENTION

The present invention provides the crystalline base of escitalopram with the formula (I):

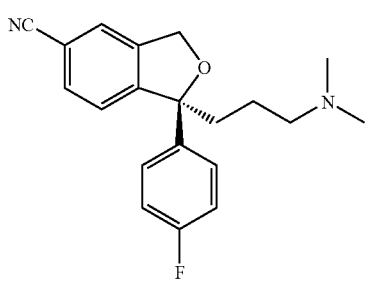

(I)

In a second aspect, the invention provides a process for the manufacture of escitalopram free base or a salt thereof, preferably the oxalate, in which escitalopram hydrobromide is precipitated in crystalline form from a solvent and separated from the solvent, optionally re-crystallised one or more times and then transformed into escitalopram free base or a pharmaceutically acceptable salt thereof provided that the escitalopram salt manufactured is not the hydrobromide.

In a third aspect, the invention relates to the pure crystalline escitalopram free base or escitalopram oxalate prepared by the above process of the invention.

In a fourth aspect, the invention provides a process for the manufacture of a salt of escitalopram, preferably the oxalate, in which the free base of escitalopram is precipitated in solid form from a solvent and separated from the solvent, optionally re-crystallised one or more times and then transformed into a pharmaceutically acceptable salt of escitalopram.

In a fifth aspect, the invention relates to the pure crystalline escitalopram oxalate prepared by the above process of the invention.

In a sixth aspect, the invention relates to a process for the reduction of the amount of escitalopram, N-oxide ((S)-1-(3-dimethylamino-propyl)-1-(4-fluoro-phenyl)-1,3-dihydro-isobenzofuran-5-carbonitrile, N-oxide) in escitalopram free base or a salt thereof comprising dissolving escitalopram free base in diethylether and removing escitalopram, N-oxide as a solid material.

In a seventh aspect, the invention relates to an orodispersible tablet having a hardness of at least 22 N and an oral-disintegration time of less than 120 s and comprising an active pharmaceutical ingredient adsorbed onto a water soluble filler, one or more disintegrants and optionally additional water soluble filler, wherein said active pharmaceutical ingredient has a melting point in the range of 40-100° C.

In an eighth aspect, the invention relates to a method of manufacture of an orodispersible tablet as described above comprising:

a) mixing the water-soluble filler and the active pharmaceutical ingredient at a temperature above, around or slightly below the melting point of the active pharmaceutical ingredient, whereby the active pharmaceutical ingredient is adsorbed onto the water-soluble filler;

b) followed by cooling to a temperature below 40° C.;

c) mixing the mixture of the active pharmaceutical ingredient and the water-soluble filler with one or more disintegrants and optionally other excipients;

pressing the mixture into tablets with a hardness of at least 22 N.

In a ninth aspect, the invention relates to pharmaceutical formulations comprising escitalopram base in solid form.

DETAILED DESCRIPTION OF THE INVENTION

In one embodiment, the invention relates to escitalopram free base in solid form, in particular in a solid form comprising crystalline escitalopram free base, and more particularly in a solid form that is at least 90% crystalline, even more particularly at least 95% crystalline and most particularly at least 98% crystalline. Specifically, the invention relates to crystalline escitalopram free base.

In one particular embodiment, the invention relates to an orodispersible tablet comprising escitalopram free base, whereas in another equally particular embodiment, the invention relates to a pharmaceutical composition containing the escitalopram free base in solid form as disclosed above. Particularly the pharmaceutical composition is for oral administration. The pharmaceutical composition according to the invention may be prepared by direct compression of escitalopram in admixture with conventional excipients. Alternatively, a wet granulate or a melt granulate of escitalopram, optionally in admixture with conventional excipients may be used for compression of tablets.

In yet another embodiment, the invention relates to a method for the manufacture of escitalopram free base or a salt thereof characterised in that escitalopram hydrobromide is precipitated in crystalline form from a solvent and separated from the solvent, optionally re-crystallised one or more times, and then transformed into escitalopram free base or a salt thereof provided that the escitalopram salt manufactured is not the hydrobromide.

In a particular embodiment, the invention relates to such a method wherein the escitalopram hydrobromide is precipitated from a crude escitalopram.

In another particular embodiment, the invention relates to such a method wherein one or more impurities of the formulas (II) or (III)

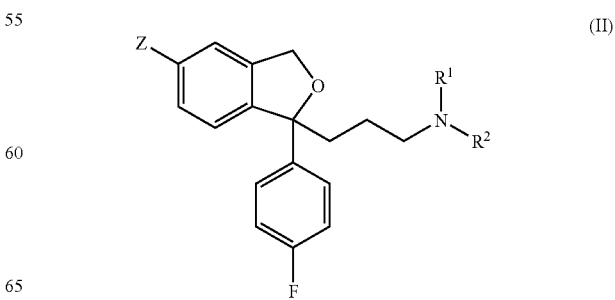

(II)

-continued

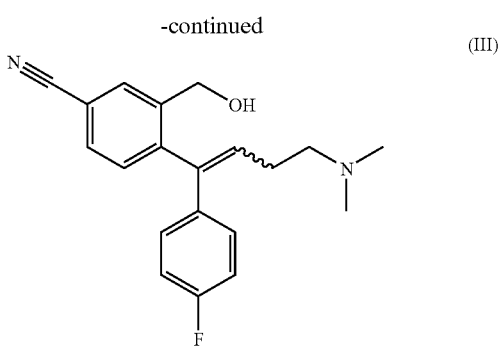

(III)

wherein Z is halogen, cyano or —$CONH_2$, $R^1$ and $R^2$ independently are hydrogen or methyl, provided that if both of $R^1$ and $R^2$ are methyl, then Z can not be cyano, and the bond drawn as a zigzag line in formula (III) indicates that the configuration around the double bond may be E- or Z-, are removed from or reduced in the escitalopram by the process. More particularly the invention relates to such a method, wherein the impurities are of formula (II) wherein Z is bromo or chloro and $R^1$ and $R^2$ are methyl, Z is —$CONH_2$ and $R^1$ and $R^2$ are methyl, or Z is cyano, $R^1$ is hydrogen and $R^2$ is methyl; or wherein the impurities are of the formula (III) wherein the configuration around the double bond is Z.

Throughout this specification with claims, the compounds of formula (II) may have the S-configuration, the R-configuration, be racemic or any mixture thereof.

Throughout this specification with claims, the terms "escitalopram oxalate" and "escitalopram hemioxalate" both refer to the same 1:1 salt between escitalopram and oxalic acid.

In another particular embodiment, the invention relates to such a method, wherein the crude escitalopram is subjected to initial purification before the escitalopram hydrobromide is precipitated in crystalline form.

In yet another particular embodiment, the invention relates to such a method, wherein the escitalopram hydrobromide is transformed into escitalopram free base or escitalopram oxalate.

In another embodiment, the invention relates to a crystalline base of escitalopram, or an oxalate salt of escitalopram prepared by a process as described above; in particular such a base or oxalate salt which contains less than 0.2% impurities other than R-citalopram, more particularly less than 0.1%. Particularly, the invention relates to a crystalline base or oxalate salt as disclosed above which contains less than 0.1% of any particular impurity other than R-citalopram.

In another embodiment, the invention relates to a crystalline base of escitalopram, or an oxalate salt of escitalopram, characterised in that it contains less than 0.2% of impurities other than R-citalopram, particularly less than 0.1%. In a particular embodiment, the invention relates to a crystalline base or oxalate salt as disclosed above which contains less than 0.1% of any particular impurity other than R-citalopram.

Throughout this specification and the claims contents of impurities are given as area % as determined by HPLC.

In yet another embodiment, the invention relates to a method for the manufacture of a salt of escitalopram characterised in that escitalopram free base is precipitated in solid form from a solvent and separated from the solvent, optionally re-crystallised one or more times, and then transformed into a salt of escitalopram.

In a particular embodiment, the invention relates to such a method wherein the escitalopram free base is precipitated from a crude escitalopram.

In another particular embodiment, the invention relates to such a method wherein one or more impurities of the formula (II)

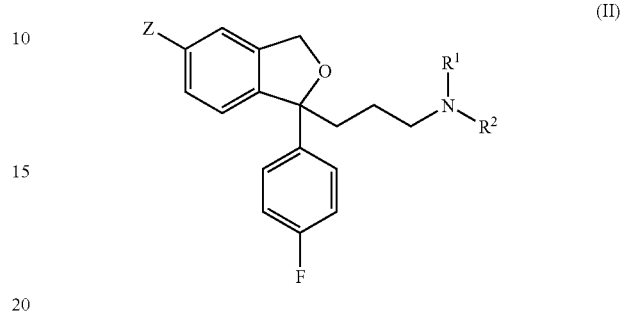

(II)

wherein Z is halogen or —$CONH_2$ are removed from or reduced in the escitalopram by the process; more particularly such a method wherein Z is bromo.

In another particular embodiment, the invention relates to such a method wherein the crude escitalopram is subjected to initial purification before the escitalopram free base is precipitated in solid form.

In yet another particular embodiment, the invention relates to such a method wherein the escitalopram free base is transformed into escitalopram oxalate.

In another embodiment the invention relates to an orodispersible tablet having a hardness of at least 22 N and an oral-disintegration time of less than 120 s and comprising an active pharmaceutical ingredient adsorbed onto a water soluble filler, one or more disintegrants and optionally additional water soluble filler, wherein said active pharmaceutical ingredient has a melting point in the range of 40-100° C., particularly in the range of 40-90° C., more particularly 40-80° C., and most particularly 45-70° C.

In a particular embodiment the invention relates to such an orodispersible tablet wherein the active pharmaceutical ingredient is selected from the group consisting of escitalopram, ethosuximide, trimethadione, chlorambucil, disulfuram, fenofibrate, guaifenesin, lomustine, carisoprodol and perphenazine and more particularly wherein the active pharmaceutical ingredient is escitalopram.

In another particular embodiment the invention relates to such an orodispersible tablet wherein the water-soluble filler is selected from the group consisting of: monosaccharides, disaccharides, sugar alcohols and polysaccharides; and more particularly wherein the water-soluble filler is selected from the group consisting of: mannitol, sorbitol, glucose, mannose and lactose.

In another particular embodiment the invention relates to such an orodispersible tablet comprising an antioxidant such as a $C_{1-6}$-alkyl gallate, e.g. propyl gallate, as an intra- or extragranular excipient.

In another particular embodiment the invention relates to such an orodispersible tablet which has a hardness of at least 22 N, particularly at least 25 N, more particularly at least 30 N, even more particularly at least 40 N, and most particularly at least 60 N. Suitably the tablet has a hardness in the range of 22-125 N, particularly 25-125 N, more particularly 30-125 N, even more particularly 40-125 N, and most particularly 60-125 N. Evenly suitably the tablet has a hardness in the range of 22-100 N, particularly 30-100 N, more particularly 40-100 N, even more particularly 25-60 N, and most particularly 30-60 N.

In another particular embodiment, the invention relates to such an orodispersible tablet, which has an oral-disintegration time of less than 60 s, particularly less than 40 s, and more particularly less than 30 s.

In another particular embodiment, the invention relates to such an orodispersible tablet, which has a friability of no more than 1%, in particular no more than 0.8%.

Disintegrants suitable to be used in the orodispersible tablets described above are selected from the group consisting of: Microcrystalline cellulose (cellulose), sodium starch glycolate (sodium carboxymethyl starch), croscarmellose sodium (cellulose, carboxymethyl ether, sodium salt, crosslinked), crospovidone (polyvinylpolypyrrolidone), povidone (polyvinyl-pyrrolidone), natural starches such as maize starch and potato starch, pregelatinized starch, compressible starch, alginic acid, sodium alginate and polacrilin potassium (2-methyl-2-propenoic acid polymer with divinyl-benzene, potassium salt); and in particular from the group consisting of: Microcrystalline cellulose, sodium starch glycolate, croscarmellose sodium, crospovidone and povidone. Most particularly the disintegrant is a croscarmellose sodium product which may provide a more stable product compared with other disintegrants.

In yet another embodiment, the invention relates to a method of manufacture of an orodispersible tablet as described above wherein said method comprises:
 a) mixing the water-soluble filler and the active pharmaceutical ingredient at a temperature above, around or slightly below the melting point of the active pharmaceutical ingredient, whereby the active pharmaceutical ingredient is adsorbed onto the water-soluble filler;
 b) followed by cooling to a temperature below 40° C., in particular below 35° C. and more particularly below 30° C.;
 c) mixing the mixture of the active pharmaceutical ingredient and the water-soluble filler with one or more disintegrants and optionally other excipients;

pressing the mixture into tablets with a hardness of at least 22 N.

Throughout the description and claims the term "cooling" comprises active and passive cooling.

The use of tableting punches with a surface comprising chromium nitride for the tableting process may be advantageous in order to reduce adhesion to the punches. Such tableting punches may be prepared by ion beam enhanced deposited coating available from BeamAlloy Technologies LLC.

In a particular embodiment, the mixing in step a) above is performed at a temperature above the melting point of the active ingredient.

The melting point is preferably within a range from 44-49° C., most preferably 45-48° C. (DSC; onset).

The terms "crude escitalopram", "crude salt" and "crude mixture" refer to the fact that the salt and the mixture, respectively, comprise impurities, in particular impurities of formula (II), which must be removed or which it is desired to remove.

The crude salt may have been separated directly from the reaction mixture, or the crude reaction mixture may have been subjected to some initial purification, e.g. one re-crystallisation, and/or treatment with activated carbon and/or silica gel, and the salt formed subsequently by treatment with an acid using methods known in the art. The salt may be isolated by precipitation or it may exist in a solvent, e.g. in the mixture resulting directly from the synthesis of the salt.

Similarly, the crude mixture comprising escitalopram may be obtained directly from the synthesis of the compound according to any of the above mentioned processes or it may have been subjected to some initial or simultaneous purification, e.g. one re-crystallisation, and/or treatment with activated carbon and/or silica gel.

The base of escitalopram may be set free from the crude salt by dissolving the crude salt in a mixture of water and an organic solvent and then adding a base to pH 7 or more. The organic solvent may be toluene, ethyl acetate, diethyl ether, methyl-tert-butyl ether, diisopropyl ether, hexane, heptane, cyclohexane, methylcyclohexane or any other suitable solvent as well as mixtures thereof and the base may be any convenient base, preferably NaOH or $NH_3$. Likewise, the base of escitalopram may, if necessary, be set free from a crude mixture containing escitalopram by treatment with a base.

Crude mixtures containing escitalopram base may be subjected to further purification and extraction before the base is precipitated in crystalline form. The base of escitalopram may be isolated by separation of the organic phase from the aqueous phase, evaporation of the solvent in order to obtain the base most probably as an oil and then crystallisation of the base from a solvent, such as an alkane, including n-heptane, hexane, isooctane, cyclohexane and methylcyclohexane, 2-methyl-tetrahydrofuran; 1-pentanol and high and low boiling petroleum ethers or mixtures thereof; as well as mixtures of one or more of the above mentioned solvents with more polar solvents such as ethyl acetate, isopropylacetate, butylacetate, acetonitrile, tetrahydrofuran and alcohols such as 2-butanol or 2-propanol, and separating the escitalopram base from the solvent. Crystalline escitalopram base may be re-crystallised from the same solvents. Crystallisation may be initiated by seeding with crystalline escitalopram oxalate or crystalline escitalopram free base.

Pharmaceutically acceptable salts of escitalopram, such as the oxalate, may be prepared by methods known in the art. So, the base may be reacted with either the stoichiometric amount of acid in a water miscible solvent, such as acetone or ethanol, with subsequent isolation of the salt by concentration and cooling, or with an excess of the acid in a water immiscible solvent, such as diethyl ether, ethyl acetate or dichloromethane, with the salt separating spontaneously. The escitalopram free base or escitalopram oxalate obtained by the method of the invention has a very high purity and contains less than 0.20% impurities other than R-citalopram, particularly less than 0.10%. In particular, the escitalopram free base or escitalopram oxalate obtained by the method of the invention contains less than 0.10% of any particular impurity other than R-citalopram. Other salts of escitalopram may also be obtained in a very pure form by this process.

The compounds of formula (II) may be prepared as described in DE 2,657,013, WO 0011926 and WO 0013648, WO 9819513, WO 9819512 and WO 9900548.

Throughout this specification with claims, the term "solid form" refers to any solid form exemplified by crystalline form, amorphous solid form, glassy form, foam as well as mixtures thereof.

Throughout this specification with claims, melting points are measured using Differential Scanning Calorimetry (DSC). The equipment used is a TA-Instruments DSC-Q1000 calibrated at 5° C./min to give the melting point as onset value. About 2 mg of sample is heated 5° C./min in a loosely closed pan under nitrogen flow.

Throughout this specification with claims, halogen means chloro, bromo or iodo. Throughout this specification with claims, the term "orodispersible tablets" refers to uncoated tablets intended to be placed in the mouth where they disperse rapidly before being swallowed. Orodispersible tablets disintegrate within 3 min when examined by the test for disintegration of tablets and capsules described in section 2.9.1 in European Pharmacopoeia 5.1, $5^{th}$ edition 2005.

Throughout this specification with claims, the term "hardness" refers to the "resistance to crushing of tablets" as defined in section 2.9.8 in European Pharmacopoeia 5.1, $5^{th}$ edition 2005. Hardness may be measured inter alia in Newton (N) or kilopond (kP). 1 kP=9.807 N.

Throughout this specification with claims, the term "friability" has the meaning defined in section 2.9.7 in European Pharmacopoeia 5.1, $5^{th}$ edition 2005.

Throughout this specification with claims, the term "water-soluble" refers to substances that are soluble, freely soluble or very soluble in water as defined in European Pharmacopoeia 5.1, $5^{th}$ edition 2005. That is "water-soluble" refers to substances where 1 g is soluble in less than 30 ml of water. In particular it refers to such substances that are freely soluble or very soluble in water. That is substances where 1 g is soluble in less than 10 ml of water.

Throughout this specification with claims, the term "disintegrant" refers to agents added to tablet granulation for the purpose of causing the compressed tablet to break apart (disintegrate) when placed in an aqueous environment.

In one particular embodiment, the invention relates to an orodispersible tablet comprising escitalopram free base, whereas in another equally particular embodiment the pharmaceutical compositions of the invention may be administered in any suitable way and in any suitable form, for example orally in the form of tablets, capsules, powders or syrups, or parenterally in the form of usual sterile solutions for injection. Preferably the pharmaceutical compositions of the invention are administered orally.

In one particular embodiment, the invention relates to an orodispersible tablet comprising escitalopram free base, whereas in another equally particular embodiment pharmaceutical formulations comprising escitalopram free base of the invention may be prepared by conventional methods in the art. For example, tablets may be prepared by mixing the active ingredient with ordinary excipients and subsequently compressing the mixture in a conventional tableting machine. Examples of excipients comprise: microcrystalline cellulose, dibasic calcium phosphate, mannitol, maize starch, potato starch, talcum, magnesium stearate, gelatine, lactose, gums, and the like. Any other excipients such as colourings, aroma, preservatives etc. may be used provided that they do not reduce the shelf life of the tablets. Preferred excipients do not adversely affect the stability of the active ingredients in the formulation.

In one particular embodiment, the invention relates to an orodispersible tablet comprising escitalopram free base, whereas in another equally particular embodiment, the formulations according to the invention may be prepared by direct compression of escitalopram in admixture with conventional excipients. Alternatively, a wet granulate or a melt granulate of escitalopram, optionally in admixture with conventional excipients may be used for compression of tablets.

Solutions for injections may be prepared by dissolving the active ingredient and possible additives in a part of the solvent for injection, preferably sterile water, adjusting the solution to the desired volume, sterilisation of the solution and filling in suitable ampoules or vials.

Any suitable additive conventionally used in the art may be added, such as tonicity agents, preservatives, antioxidants, solubility enhancing agents etc.

According to the present invention, the base of escitalopram has been found to be crystalline with stable white crystals and it has been found that the base may be crystallised easily in a very pure form. So for example pure escitalopram base containing less than 0.2% of impurities different from R-citalopram, particularly less than 0.1% was obtained by crystallisation from at least 95% pure escitalopram hydrobromide without further purification. In a particular embodiment, pure escitalopram base that contains less than 0.1% of any particular impurity was obtained. Accordingly, the process of the invention for preparing salts of escitalopram has been found to give the salts as very pure products of pharmaceutically acceptable quality. Accordingly, the yield may be improved substantially during the manufacture of escitalopram.

Melt agglomeration is an agglomeration process whereby a molten binder liquid is used. The molten binder solidifies at room temperature. One such binder is referred to as meltable binder. In a melt agglomeration process, the process is usually conducted at elevated temperatures. The process temperature can be similar to the temperature at which the binder melts, but it can also be higher and even below the melting point. Once the process temperature reach the level that causes melting or softening of the binder, the binder aid the formation and growth of agglomerates. During the agglomeration process the temperature may be non-uniform in the mixture due to local friction forces resulting in local friction heating. This results in that part of the binder may be solid whereas other parts may be melted or softened. The agglomeration process may proceed by either the distribution mechanism, the immersion mechanism or by a combination of the two mechanisms. When agglomerates of the desired size are formed, the agglomerates are cooled to a temperature below 40° C. whereby the molten or softened binder congeals. The agglomerates can, subsequently, be mixed with excipients prior to compression into tablets.

The process may also be conducted so that agglomeration does not take place. In that case, the process could be termed a melt coating process. The procedure is similar to the one described for melt agglomeration. The only difference is that the coating material, i.e. the meltable binder, will distribute over the filler particles resulting in a more or less homogeneous coating layer. To avoid agglomeration, the processing conditions or the amount of coating material, i.e. meltable binder relative to the amount of filler particles must be controlled. The coated filler particles can subsequently be mixed with excipients prior to compression into tablets.

The meltable binder used in melt agglomeration is usually polyethylene glycols, fatty acids, fatty alcohols or glycerides. It has now been found that pharmaceutically active substances with a suitable melting point may be used as a meltable binder in a melt agglomeration process. Suitable melting points are in the range of 40-100° C.

In one embodiment, the agglomerate or coated filler particle is prepared by melting the active pharmaceutical ingredient and spraying or pouring the melt on the filler. The spraying or pouring step may be performed in accordance with known procedures.

In another embodiment all constituents of the agglomerate or coated filler particle are added to a high shear mixer, optionally provided with a heating jacket. By operating the high shear mixer the friction heat and/or heat supplied by the heating jacket will melt the active pharmaceutical ingredient which deposits onto the filler. This method is a very attractive method for melt agglomeration, because the method is fast and easy to perform.

Melt extrusion is a process wherein the low melting point compound and the filler are mixed and heated in a mixer that is usually part of the extruder. The soft mass is then fed to the extrusion chamber and forced through small holes or orifices to shape it into thin rods or cylinders. The melt extrusion process may alternatively be conducted by mixing the low melting compound and the filler in an unheated mixer. The mixture is, subsequently, transferred to a heated extruder. In the heated extruder, the low melting compound melts and enables the formation of soft mass in the extrusion chamber. The soft mass is forced through small holes or orifices to shape it into thin rods or cylinders. After the extruded material congeals it can be milled or spheronized using standard equipment.

Agglomerates, coated filler particles or extrudates according to the invention may be prepared using procedures and apparatus known within the art for melt agglomeration.

Exemplary of apparatus, which may be used are low shear mixers, high shear mixers, fluid beds, fluid bed granulators, rotary fluidised beds and drum granulators.

Prior to tablet production, prestart operations is required to establish the compression force needed to compress tablets of the desired hardness, friability etc. Those skilled in the art will know how to adjust the compression force in order to obtain the desired hardness and/or friability. It is, however, known for the skilled people within the art, that the compressibility of the formulation determines what tablet hardness can be achieved by a given compression force.

The invention is further illustrated by the following examples.

HPLC analyses were performed on a Luna $C_{18}$, (2) 250× 4.6 mm, ID 5 μm column with gradient eluation using mobile phase A (25 mM aqueous phosphate buffer pH 3.0/acetonitrile (90:10)) and mobile phase B (25 mM aqueous phosphate buffer pH 3.0/acetonitrile (35:65)) with UV detection at 224 nm. A column temperature of 45° C. was used, and injection volumes were 20 μL. Runtime was 65 min with the following gradient profile:

| Time (min) | Phase A (%) | Phase B (%) | Flow (ml/min) |
| --- | --- | --- | --- |
| 0.0 | 95 | 5 | 1.0 |
| 35.0 | 65 | 35 | 1.0 |
| 45.0 | 0 | 100 | 1.0 |
| 45.1 | 0 | 100 | 2.0 |
| 60.0 | 0 | 100 | 1.0 |
| 60.1 | 95 | 5 | 1.0 |
| 65.0 | 95 | 5 | 1.0 |

Results were reported as area %. Standards were used only for the identification of the mentioned compounds.

EXAMPLE 1

Liberation of Escitalopram Free Base from Escitalopram Oxalate 704 g of escitalopram oxalate was placed in a 6 L three-necked flask equipped with mechanical stirrer and pressure-equalising funnel. 3 L of water was added followed by 600 mL of diethyl ether. pH was adjusted to 9-9.5 by addition of 27% w/w aqueous ammonia and the mixture was stirred for ½ hour. The phases were separated and the water phase was extracted once more with 300 mL of diethyl ether. The combined organic phases were washed twice with 300 mL water, dried over $MgSO_4$, filtered and evaporated under vacuum at 40° C. to give a light brown oil.

Yield: 542.5 g (98.4%)

EXAMPLE 2

Precipitation of Escitalopram Hydrobromide, Liberation of the Free Base and Crystallisation of the Base Precipitation of the Escitalopram Hydrobromide Salt:

3 kg of escitalopram free base (purity by HPLC: 99.16% (area %)) as a light brown oil dissolved in 12 kg of 2-propanol was charged into a 20 L thermostatically controlled reactor with mechanical stirring, reflux condenser, scrubber, gas-inlet and thermometer. The solution was heated to 40° C. and HBr gas was bubbled through the solution until pH was between 3 and 4. This reaction was exothermic and the temperature in the reactor was kept between 40 and 43° C. A small amount of seeding crystals (escitalopram hydrobromide, 100-200 mg) was added and crystallisation started within 10 minutes. The mixture was then slowly cooled to 10° C. over 5 hours and kept at this temperature for an additional 12 hours. The crystals were filtered off, rinsed on the filter with 3×1 L 2-propanol and dried to constant weight under vacuum at 60° C.

Yield: 3.49 kg (93%)

Purity of the product by HPLC: 99.86% (area %)

Liberation of the Free Base:

650 g of escitalopram hydrobromide (purity by HPLC (the hydrobromide salt): 99.86% by area %) was placed in a 4 L three-necked flask equipped with mechanical stirrer and pressure-equalising funnel. 2 L of water was added followed by 1 L of diethyl ether. pH was adjusted to 9-9.5 by addition of 27% w/w aqueous ammonia and the mixture was stirred for ½ hour. The phases were separated and the water phase was extracted once more with 500 mL of diethyl ether. The combined organic phases were washed twice with 300 mL water, dried over $MgSO_4$, filtered and evaporated under vacuum at 40° C. to give a light brown oil.

Yield: 520 g (100%)

Crystallisation of the Free Base:

The escitalopram free base was transferred to a 2 L thermostatically controlled reactor equipped with mechanical stirrer, reflux condenser, $N_2$ in/out and a thermometer. 50 mL of ethyl acetate was added followed by 1.3 L heptane. The mixture was heated to 40° C. to form a homogeneous solution. Hereafter, a slow cooling to −5° C. over 12 hours was begun and when the temperature was about 20° C. the mixture was seeded with a small amount of escitalopram oxalate (10-20 mg). Crystallisation of the free base started after about ½ hour. The mixture was then stirred for 5 hours at −5° C., the crystals were filtered off, rinsed on the filter with 2×150 mL heptane and dried under vacuum at 25° C. to constant weight.

Yield: 432 g (83%)

Purity of the product by HPLC: 99.95% (area %)

Melting point (DSC, onset): 46.6° C.

EXAMPLE 3

Crystallisation of Escitalopram Free Base 520 g of escitalopram free base as a light brown oil (Purity: 99.25%; HPLC) was placed in a 2 L thermostatically controlled reactor equipped with mechanical stirrer, reflux condenser, $N_2$ in/out and a thermometer. 50 mL of ethyl acetate was added and the mixture was heated to 35° C. whereupon 1.3 L heptane was added. When the solution was homogeneous a slow cooling to −5° C. over 12 hours was begun. When the temperature was 20° C., a small amount (10-20 mg) of seeding crystals (Escitalopram base) were added. Crystallization started around 10° C. The mixture was stirred at −5° C. for an additional 5-7 hours whereafter the crystals were removed by filtration. The crystals were washed on the filter with 2×150 mL of heptane and dried under vacuum at 25° C. to constant weight.

Yield: 485 g (93.3%)
Purity of product by HPLC: 99.58% (area %)
Melting point (DSC, onset): 45.8° C.

EXAMPLE 4

Purification of Escitalopram by Precipitation of Escitalopram Free Base or Hydrobromide A stock solution of escitalopram (free base, oil) in ethanol was used. The ethanol was removed under reduced pressure, and 400 g of the resulting oil was measured into a flask, where the following were added: 2 g of the 5-amido analogue of citalopram ((R,S)-1-(3-dimethylamino-propyl)-1-(4-fluoro-phenyl)-1,3-dihydro-isobenzofuran-5-carboxylic acid amide), 2 g of the 5-bromo analogue of citalopram ((R,S)-{3-[5-bromo-1-(4-fluoro-phenyl)-1,3-dihydro-isobenzofuran-1-yl]-propyl}-dimethyl-amine) and 2 g of the desmethyl analogue of citalopram ((R,S)-1-(4-fluoro-phenyl)-1-(3-methylamino-propyl)-1,3-dihydro-isobenzofuran-5-carbonitrile). The resulting mixture (S0) was dissolved in ethyl acetate to 1000 mL, and divided into 4 equal parts, and each were evaporated separately to give an oil.

The four parts were each sequentially crystallized according to the below scheme and procedures:

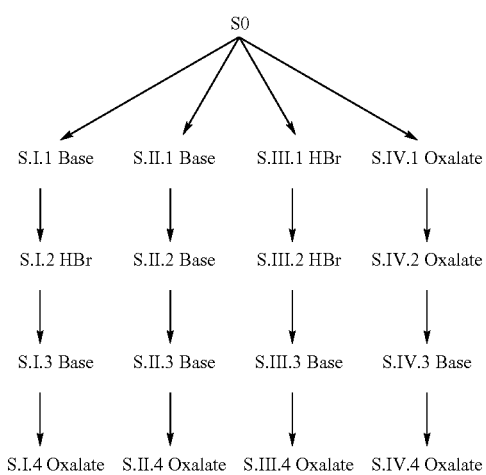

Precipitation of the Crystalline Free Base:
100 g of the free base was dissolved in 10 mL of ethyl acetate and 240 mL of heptane at 40° C. The mixture was allowed to cool to room temperature where the mixture was seeded with crystalline escitalopram free base. The mixture was then cooled to ca. 0° C. and stirred for ca. 2 hours, the crystals were filtered off, rinsed on the filter with heptane and dried under vacuum at 25° C. to constant weight.

Recrystallization of the free base followed the same procedure as precipitation of the free base.

Precipitation of the Escitalopram Hydrobromide Salt:
100 g of the free base was dissolved in 250 mL of 2-propanol. Hydrogen bromide (anhydrous) in 2-propanol was added until a pH of 3.5-4 was obtained and the volume was adjusted to 400 mL with 2-propanol. The crystallization started within 10 minutes. The mixture was then allowed to cool to room temperature and was stirred for ca. 2 hours. The crystals were filtered off, rinsed on the filter with 2-propanol and dried to constant weight under vacuum at 60° C.

Recrystallization of the Escitalopram Hydrobromide Salt:
100 g escitalopram hydrobromide was dissolved in 500 mL of 2-propanol at 70° C. The mixture was allowed to cool to room temperature. The crystals were filtered off, rinsed on the filter with 2-propanol and dried to constant weight under vacuum at 60° C.

Precipitation of the Escitalopram Oxalate Salt:
100 g of the free base was dissolved in 250 mL of 2-propanol. 1 eq. of oxalic acid dihydrate was dissolved in 250 mL of warm 2-propanol and was added at 40° C. to the solution of escitalopram base. After stirring at 40° C. for 10 min the crystallization started. The mixture was then allowed to cool to room temperature and stirred for ca. 2 hours. The crystals were filtered off, rinsed on the filter with 2-propanol and dried to constant weight under vacuum at 60° C.

Recrystallization of the Escitalopram Oxalate Salt:
100 g escitalopram oxalate was dissolved in 1250 mL ethanol at reflux. The mixture was allowed to cool to room temperature. The crystals were filtered off, rinsed on the filter with ethanol and dried to constant weight under vacuum at 60° C.

Liberation of the Free Base:
100 g escitalopram hydrobromide or oxalate was dissolved or suspended in water and ethyl acetate was added. pH was adjusted to 9-9.5 by addition of 27% w/w aqueous ammonia and the mixture was stirred for ½ hour. The phases were separated and the water phase was extracted once more with ethyl acetate. The combined organic phases were washed with water, dried over $MgSO_4$, filtered and evaporated under vacuum at 40° C. to give a light brown oil.

After each precipitation or crystallization a sample was taken which was analysed for overall purity and the content of the 5-amido analogue of citalopram, the 5-bromo analogue of citalopram and the desmethyl analogue of citalopram. The results are given in % in table 1. All the products were crystalline unless otherwise stated.

TABLE 1

| Sample | Form | Purity | 5-amido analogue | 5-bromo analogue | desmethyl analogue |
|---|---|---|---|---|---|
| S.0 | Base (Oil) | 97.63 | 0.52 | 0.50 | 0.47 |
| S.I.1 | Base | 98.51 | 0.48 | 0.44 | 0.13 |
| S.I.2 | HBr | 99.50 | 0.07 | 0.21 | 0.06 |
| S.I.3 | Base | 99.65 | 0.06 | 0.20 | 0.03 |

TABLE 1-continued

| Sample | Form | Purity | 5-amido analogue | 5-bromo analogue | desmethyl analogue |
|---|---|---|---|---|---|
| S.I.4 | Oxalate | 99.60 | 0.05 | 0.17 | 0.03 |
| S.0 | Base (Oil) | 97.63 | 0.52 | 0.50 | 0.47 |
| S.II.1 | Base | 98.55 | 0.42 | 0.42 | 0.14 |
| S.II.2 | Base | 98.71 | 0.43 | 0.42 | 0.07 |
| S.II.3 | Base | 98.78 | 0.45 | 0.40 | 0.04 |
| S.II.4 | Oxalate | 98.87 | 0.41 | 0.37 | 0.04 |
| S.0 | Base (Oil) | 97.63 | 0.52 | 0.50 | 0.47 |
| S.III.1 | HBr | 99.34 | 0.10 | 0.23 | 0.16 |
| S.III.2 | HBr | 99.65 | 0.02 | 0.15 | 0.06 |
| S.III.3 | Base | 99.71 | 0.017 | 0.16 | 0.03 |
| S.III.4 | Oxalate | 99.70 | 0.015 | 0.10 | 0.03 |
| S.0 | Base (Oil) | 97.63 | 0.52 | 0.50 | 0.47 |
| S.IV.1 | Oxalate | 98.06 | 0.45 | 0.42 | 0.48 |
| S.IV.2 | Oxalate | 98.81 | 0.20 | 0.21 | 0.47 |
| S.IV.3 | Base | 99.42 | 0.16 | 0.165 | 0.13 |
| S.IV.4 | Oxalate | 99.34 | 0.15 | 0.15 | 0.13 |

EXAMPLE 5

Purification of Escitalopram by Precipitation of Escitalopram Free Base or Hydrobromide

| Sample # Enantiomer | Type | 5-Amido Lu 14-017 (S) | Desmethyl Lu 11-109 (S) | 5-Chloro Lu 10-134 (S) | 5-Bromo Lu 10-132 (S) | Escitalopram LC-MS purity (%) |
|---|---|---|---|---|---|---|
| T.0 | Crude | 0.73 | 0.753 | 0.165 | 0.291 | 97.59 |
| T.I | hemi-Oxalate | 0.253 | 0.274 | 0.167 | 0.289 | 98.89 |
| T.II | Recryst. ox. | 0.13 | 0.114 | 0.164 | 0.276 | 99.27 |
| T.III.1 | Base | 0.118 | 0.115 | 0.091 | 0.166 | 99.51 |
| T.IV.1 | hemi-Oxalate | 0.078 | 0.059 | 0.069 | 0.133 | 99.66 |
| T.0 | Crude | 0.73 | 0.753 | 0.165 | 0.291 | 97.59 |
| T.I | hemi-Oxalate | 0.253 | 0.274 | 0.167 | 0.289 | 98.89 |
| T.II | Recryst. ox. | 0.13 | 0.114 | 0.164 | 0.276 | 99.27 |
| T.III.2 | HBr salt | 0.022 | 0.064 | 0.078 | 0.137 | 99.67 |
| T.IV.2 | hemi-Oxalate | 0.014 | 0.037 | 0.073 | 0.126 | 99.76 |

Crude escitalopram base (oil, 20.7 g) (T.0) (purity: 97.59% measured by LC-MS against standards) containing the four impurities 5-amido analogue of escitalopram ((S)-1-(3-dimethylamino-propyl)-1-(4-fluoro-phenyl)-1,3-dihydro-isobenzofuran-5-carboxylic acid amide) (0.73%); desmethyl analogue of escitalopram ((S)-1-(4-fluoro-phenyl)-1-(3-methyl-amino-propyl)-1,3-dihydro-isobenzofuran-5-carbonitrile) (0.753%); 5-chloro analogue of escitalopram ((S)-{3-[5-chloro-1-(4-fluoro-phenyl)-1,3-dihydro-isobenzofuran-1-yl]-propyl}-dimethyl-amine) (0.165%); 5-bromo analogue of escitalopram ((S)-{3-[5-bromo-1-(4-fluoro-phenyl)-1,3-dihydro-isobenzofuran-1-yl]-propyl}-dimethyl-amine) (0.291%)) as described in the above schemes was purified in different ways.

A hemi-oxalate salt of escitalopram was precipitated from IPA (2-propanol, 150 mL) and oxalic acid, $2H_2O$ (8.0 grams) (T.I, 26.0 g). The hemi oxalate salt (T.I, 26.0 g) was recrystallized from IPA (250 mL) (T.II, 24.3 g)

From (T.II, 20 g) escitalopram base was liberated and isolated as an oil (15.4 g). About half the amount of this base (7.8 g) was precipitated as the crystalline base from (n-heptane/ethyl:acetate (95:5), 8.5 mL) (T.III.1, 7.0 g). The other half (7.6 g) was dissolved in IPA (60 mL) and by adding HBr (HBr in IPA: 0.12 g HBr/mL; 16.6 mL) escitalopram hydrobromide was precipitated and isolated in crystalline form (T.III.2, 8.53 g).

(T.III.1, 6.91 g) was dissolved in IPA (70 mL) and oxalic acid, $2H_2O$ (2.82 g) was added. The hemi-oxalate of escitalopram precipitated (T.IV.1, 8.67 g). Likewise a hemi-oxalate salt of escitalopram (T.IV.2, 8.35 g) was precipitated after liberating and isolating the base (6.78 g) from (T.III.2) from IPA (70 mL) and oxalic acid, $2H_2O$ (2.77 g).

EXAMPLE 6

Reduction of the Content of Escitalopram N-oxide in Escitalopram

Escitalopram base (51.3 grams, purity 98.60% (HPLC-area %)) containing escitalopram N-oxide (0.45% by HPLC-area %) was dissolved in diethyl ether (250 mL) at room temperature. Almost immediately after the crude escitalopram was dissolved, a precipitate started to form. The suspension was stirred for three hours at 20° C. A precipitate (0.77 gram) was filtered off and identified with LC-MS to be a mixture of escitalopram base and escitalopram N-oxide in a ratio of about 2/1. The filtrate contained escitalopram base (50.5 grams, purity 99.0% (HPLC-area %)). The amount of escitalopram N-oxide in the filtrate was measured to 0.07% (HPLC-area %) relative to escitalopram base.

FORMULATION EXAMPLES

Orodispersible Tablets

EXAMPLE 7

TABLE 2

| Composition | mg/tablet |
|---|---|
| I Escitalopram base | 4.98 |
| II Mannitol (Pearlitol SD 100) | 99.57 |
| III Mannitol (Pearlitol SD 100) | 73.80 |
| IV Microcrystalline cellulose (Avicel PH 101) | 63.96 |
| V Magnesium stearate | 3.69 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler) and (V) magnesium stearate (lubricant). The mixture was split into three portions. Each portion was compressed into tablets using different compression pressures during the tabletting process. The tablet hardnesses, tablet friabilities and the disintegration times are shown in Table 3.

TABLE 3

| Compression pressure level | Tablet hardness (N) | Tablet friability (%) | Disintegration time (Min:Sec) |
|---|---|---|---|
| 1 | 67 | 0.19 | 00:26 |
| 2 | 93 | 0.09 | 00:50 |
| 3 | 103 | 0.08 | 01:26 |

EXAMPLE 8

TABLE 4

| Composition | mg/tablet |
|---|---|
| I Escitalopram base | 4.98 |
| II Mannitol (Pearlitol SD 100) | 99.57 |
| III Mannitol (Pearlitol SD 100) | 61.5 |
| IV Microcrystalline cellulose (Avicel PH 101) | 51.66 |
| V Croscarmellose sodium (Ac-Di-Sol) | 24.6 |
| VI Magnesium stearate | 3.69 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler), (V) Ac-Di-Sol (disintegrant) and (VI) magnesium stearate (lubricant). The mixture was split into three portions. Each portion was compressed into tablets using different compression pressures during the tabletting process. The tablet hardnesses, tablet friabilities and the disintegration times are shown in Table 5.

TABLE 5

| Compression pressure level | Tablet hardness (N) | Tablet friability (%) | Disintegration time (Min:Sec) |
|---|---|---|---|
| 1 | 56 | Non-detectable | 00:30 |
| 2 | 78 | Non-detectable | 00:46 |
| 3 | 107 | Non-detectable | 00:56 |

EXAMPLE 9

TABLE 6

| Composition | mg/tablet |
|---|---|
| I Escitalopram base | 5.0 |
| II Mannitol (Pearlitol SD 100) | 100.04 |
| III Mannitol (Pearlitol SD 100) | 73.80 |
| IV Microcrystalline cellulose (Avicel PH 101) | 51.17 |
| V Crospovidon (Kollidon CL) | 12.3 |
| VI Magnesium stearate | 3.69 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler), (V) crospovidon (Kollidon CL) (disintegrant) and (VI) magnesium stearate (lubricant). The mixture was split into three portions. Each portion was compressed into tablets using different compression pressures during the tabletting process. The tablet hardnesses, tablet friabilities and the disintegrating times are shown in Table 7.

TABLE 7

| Compression pressure level | Tablet hardness (N) | Tablet friability (%) | Disintegrating time (Min:Sec) |
|---|---|---|---|
| 1 | 70 | 0.11 | 00:14 |
| 2 | 90 | 0.04 | 00:21 |
| 3 | 121 | 0.007 | 00:35 |

EXAMPLE 10

TABLE 8

| Composition | mg/tablet |
|---|---|
| I Escitalopram base | 5.0 |
| II Mannitol (Pearlitol SD 100) | 100.04 |
| III Mannitol (Pearlitol SD 100) | 73.80 |
| IV Microcrystalline cellulose (Avicel PH 101) | 51.17 |
| V Primojel | 12.3 |
| VI Magnesium stearate | 3.69 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler), (V) Primojel (disintegrant) and (VI) magnesium stearate (lubricant). The mixture was split into three portions. Each portion was compressed into tablets using different compression pressures during the tabletting process. The tablet hardnesses, tablet friabilities and the disintegration times are shown in Table 9.

TABLE 9

| Compression pressure level | Tablet hardness (N) | Tablet friability (%) | Disintegration time (Min:Sec) |
|---|---|---|---|
| 1 | 64 | 0.26 | 00:20 |
| 2 | 85 | 0.19 | 00:27 |
| 3 | 103 | 0.13 | 00:40 |

EXAMPLE 11

TABLE 10

| Composition | mg/tablet |
|---|---|
| I Escitalopram base | 5.0 |
| II Mannitol (Pearlitol SD 100) | 100.04 |
| III Mannitol (Pearlitol SD 100) | 73.80 |

TABLE 10-continued

| Composition | mg/tablet |
| --- | --- |
| IV Microcrystalline cellulose (Avicel PH 101) | 51.17 |
| V Croscarmellose sodium (Ac-Di-Sol) | 12.3 |
| VI Magnesium stearate | 3.69 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler), (V) Ac-Di-Sol (disintegrant) and (VI) Magnesium stearate (lubricant). The mixture was split into three portions. Each portion was compressed into tablets using different compression pressures during the tabletting process. The tablet hardnesses, tablet friabilities and the disintegration times are shown in Table 11.

TABLE 11

| Compression pressure level | Tablet hardness (N) | Tablet friability (%) | Disintegration time (Min:Sec) |
| --- | --- | --- | --- |
| 1 | 64 | 0.16 | 00:22 |
| 2 | 87 | 0.15 | 00:31 |
| 3 | 94 | 0.11 | 00:32 |

EXAMPLE 12

TABLE 12

| Composition | mg/tablet |
| --- | --- |
| I Escitalopram base | 5.01 |
| II Mannitol (Pearlitol SD 100) | 47.52 |
| III Mannitol (Pearlitol SD 100) | 36.90 |
| IV Microcrystalline cellulose (Avicel PH 101) | 25.58 |
| V Crospovidon (Kollidon CL) | 6.15 |
| VI Magnesium stearate | 1.85 |

(I) Escitalopram base and (II) mannitol (Pearlitol SD 100) were melt agglomerated in a high shear mixer. The temperature of the heating mantle was kept at 50° C. and a mixer speed of 500 rpm was applied. The resulting mixture was mixed with (III) mannitol (extragranular filler), (IV) microcrystalline cellulose (Avicel PH101) (extragranullar filler), (V) Crospovidon (Kollidon CL) (disintegrant) and (VI) magnesium stearate (lubricant). The mixture was split into three portions. Each portion was compressed into tablets using different compression pressures during the tabletting process. The tablet hardnesses, tablet friabilities and the disintegration times are shown in Table 13.

TABLE 13

| Compression pressure level | Tablet hardness (N) | Tablet friability (%) | Disintegration time (Min:Sec) |
| --- | --- | --- | --- |
| 1 | 35 | 0.6 | 00:14 |
| 2 | 58 | 0.6 | 00:30 |
| 3 | 86 | 0.62 | 01:22 |

EXAMPLE 13

TABLE 14

| Composition | mg/tablet |
| --- | --- |
| I Escitalopram base | 5.02 |
| II Crystalline Maltitol (Maltisorb P 90) | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) crystalline maltitol (Maltisorb P 90) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was compressed into tablets. The tablet hardnesses, tablet friabilities and the disintegration times are shown in Table 15.

TABLE 15

| Compression pressure level | Tablet hardness (N) | Tablet friability (%) | Disintegration time (Min:Sec) |
| --- | --- | --- | --- |
| 1 | 24.6 | Not measured | 01:09 |

EXAMPLE 14

TABLE 16

| Composition | mg/tablet |
| --- | --- |
| I Escitalopram base | 5.02 |
| II Crystalline Dextrose monohydrate SF | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) crystalline dextrose monohydrate SF (particle size approx. 50 µm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was compressed into tablet. The tablet hardnesses, tablet friabilities and the disintegration times are shown in Table 17.

TABLE 17

| Compression pressure level | Tablet hardness (N) | Tablet friability (%) | Disintegration time (Min:Sec) |
| --- | --- | --- | --- |
| 1 | 30.5 | 0.6 | 01:11 |

EXAMPLE 15

TABLE 18

| Composition | mg/tablet |
| --- | --- |
| I Escitalopram base | 5.02 |
| II Crystalline Lactose | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) crystalline lactose (Pharmatose 125 M. Particle size approx. 55 μm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was split into two portions. Each portion was compressed into tablets using different compression pressures during the tabletting process. The tablet hardnesses, tablet friabilities and the disintegration times are shown in Table 19.

TABLE 19

| Compression pressure level | Tablet hardness (N) | Tablet friability (%) | Disintegration time (Min:Sec) |
| --- | --- | --- | --- |
| 1 | 33.5 | 0.5 | 00:37 |
| 2 | 41.7 | 0.5 | 00:34 |

EXAMPLE 16

TABLE 20

| Composition | mg/tablet |
| --- | --- |
| I Escitalopram base | 5.02 |
| II Crystalline Lactose | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) crystalline lactose (Pharmatose 110 M. Particle size approx. 105 μm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was split into three portions. Each portion was compressed into tablets using different compression pressures during the tabletting process. The tablet hardnesses, tablet friabilities and the disintegration times are shown in Table 21.

TABLE 21

| Compression pressure level | Tablet hardness (N) | Tablet friability (%) | Disintegration time (Min:Sec) |
| --- | --- | --- | --- |
| 1 | 33.3 | 0.5 | 00:38 |
| 2 | 36.3 | 0.6 | 01:03 |
| 3 | 40.4 | 0.6 | 01:20 |

EXAMPLE 17

TABLE 22

| Composition | mg/tablet |
| --- | --- |
| I Escitalopram base | 5.02 |
| II Crystalline Lactose | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) crystalline lactose (Pharmatose 90 M. Particle size approx. 135 μm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was compressed into tablets. The tablet hardnesses, tablet friabilities and the disintegration times are shown in Table 23.

TABLE 23

| Compression pressure level | Tablet hardness (N) | Tablet friability (%) | Disintegration time (Min:Sec) |
| --- | --- | --- | --- |
| 1 | 30.6 | 0.8 | 00:53 |

EXAMPLE 18

TABLE 24

| Composition | mg/tablet |
| --- | --- |
| I Escitalopram base | 5.02 |
| II Spraydried Lactose | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) spraydried lactose (Pharmatose DCL 11. Particle size approx. 110 μm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was compressed into tablets. The tablet hardnesses, tablet friabilities and the disintegration times are shown in Table 25.

TABLE 25

| Compression pressure level | Tablet hardness (N) | Tablet friability (%) | Disintegration time (Min:Sec) |
|---|---|---|---|
| 1 | 25.1 | 0.9 | 00:49 |

EXAMPLE 19

TABLE 26

| Composition | mg/tablet |
|---|---|
| I Escitalopram base | 5.02 |
| II Spraydried lactose | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Escitalopram base and (II) spraydried lactose (Pharmatose DCL 14. Particle size approx. 110 μm) were melt agglomerated in a high shear mixer. The temperature of the heating mantle was kept at 80° C. and a mixer speed of 800 rpm was applied. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was compressed into tablets. The tablet hardnesses, tablet friabilities and the disintegration times are shown in Table 27.

TABLE 27

| Compression pressure level | Tablet hardness (N) | Tablet friability (%) | Disintegration time (Min:Sec) |
|---|---|---|---|
| 1 | 24.3 | 0.8 | 01:01 |

EXAMPLE 20

TABLE 28

| Composition | mg/tablet |
|---|---|
| I Fenofibrate | 5.02 |
| II Mannitol (Pearlitol SD 100) | 100.46 |
| III Mannitol (Pearlitol SD 100) | 36.00 |
| IV Microcrystalline cellulose (Avicel PH 102) | 25.02 |
| V Croscarmellose sodium (Ac-Di-Sol) | 9.00 |
| VI Magnesium stearate | 4.5 |

(I) Fenofibrate and (II) mannitol (Pearlitol SD 100) were melt agglomerated in a high shear mixer. The temperature of the heating mantle was kept at 80° C. The resulting mixture was mixed with (III) mannitol (extragranular filler), (IV) microcrystalline cellulose (Avicel PH102) (extragranullar filler), (V) Ac-Di-Sol (disintegrant) and (VI) magnesium stearate (lubricant). The mixture was split into two portions. Each portion was compressed into tablets using different compression pressures during the tabletting process. The tablet hardnesses, tablet friabilities and the disintegration times are shown in Table 29.

TABLE 29

| Compression pressure level | Tablet hardness (N) | Tablet friability (%) | Disintegration time (Min:Sec) |
|---|---|---|---|
| 1 | 33.2 | 0.6 | 00:28 |
| 2 | 56.3 | 0.7 | 00:30 |

EXAMPLE 21

TABLE 30

| Composition | mg/tablet |
|---|---|
| I Escitalopram base | 4.99 |
| II Mannitol (Pearlitol 160C) | 99.84 |
| III Mannitol (Pearlitol 160C) | 36.40 |
| IV Microcrystalline cellulose (Avicel PH 102) | 25.30 |
| V Crospovidon (Kollidon CL) | 9.10 |
| VI Magnesium stearate | 6.37 |

(I) Escitalopram base and (II) mannitol (Pearlitol 160C. Particle size approx. 160 μm) were melt agglomerated in a high shear mixer. The temperature of the heating mantle was kept at 65° C. and a mixer speed of 500 rpm was applied. The resulting mixture was mixed with (III) mannitol (Pearlitol 160C) (extragranular filler), (IV) microcrystalline cellulose (Avicel PH101) (extragranullar filler), (V) Crospovidon (disintegrant) and (VI) magnesium stearate (lubricant). The mixture was compressed into tablets. The tablet hardnesses, tablet friabilities and the disintegration times are shown in Table 31.

TABLE 31

| Compression pressure level | Tablet hardness (N) | Tablet friability (%) | Disintegration time (Min:Sec) |
|---|---|---|---|
| 1 | 24.1 | 0.7 | 00:18 |

EXAMPLE 22

TABLE 32

| Composition | mg/tablet |
|---|---|
| I Escitalopram base | 4.99 |
| II Mannitol (Pearlitol 300DC) | 99.84 |
| III Mannitol (Pearlitol 300DC) | 36.40 |
| IV Microcrystalline cellulose (Avicel PH 102) | 25.30 |
| V Crospovidon (Kollidon CL) | 9.10 |
| VI Magnesium stearate | 6.37 |

(I) Escitalopram base and (II) mannitol (Pearlitol 300DC. Particle size approx. 300 μm) were melt agglomerated in a high shear mixer. The temperature of the heating mantle was kept at 65° C. and a mixer speed of 500 rpm was applied. The resulting mixture was mixed with (III) mannitol (Pearlitol 300DC) (extragranular filler), (IV) microcrystalline cellulose (Avicel PH101) (extragranullar filler), (V) Crospovidon (disintegrant) and (VI) magnesium stearate (lubricant). The mixture was compressed into tablets. The tablet hardnesses, tablet friabilities and the disintegration times are shown in Table 33.

TABLE 33

| Compression pressure level | Tablet hardness (N) | Tablet friability (%) | Disintegration time (Min:Sec) |
|---|---|---|---|
| 1 | 27 | 0.33 | 00:30 |

The invention claimed is:

1. A process for the reduction of the amount of escitalopram, N-oxide in escitalopram free base or a salt thereof comprising dissolving escitalopram free base in diethylether and removing escitalopram, N-oxide as a solid material.

* * * * *

UNITED STATES PATENT AND TRADEMARK OFFICE
CERTIFICATE OF CORRECTION

PATENT NO. : 7,560,576 B2  Page 1 of 1
APPLICATION NO. : 12/046984
DATED : July 14, 2009
INVENTOR(S) : Hans Petersen It is certified that error appears in the above-identified patent and that said Letters Patent is hereby corrected as shown below:

On the Title Pg, Item (75)

Please delete the following inventors:

"Robert Dancer, Hvidovre (DK)

Ole Nielsen, Valby (DK)

Michael Harold Rock, Hvidovre (DK)

Helle Eliasen, Koge (DK)

Ken Liljergen, Vaerlose (DK)"

Signed and Sealed this

Sixth Day of July, 2010

David J. Kappos
*Director of the United States Patent and Trademark Office*